United States Patent [19]

Jones et al.

[11] Patent Number: 4,699,897

[45] Date of Patent: * Oct. 13, 1987

[54] BIOLOGICALLY ACTIVE PEPTIDES STRUCTURALLY RELATED TO REGIONS WITHIN GROWTH HORMONES

[75] Inventors: Theodore Jones, Lakewood, Colo.; Christopher G. Rudman, Thousand Oaks, Calif.

[73] Assignee: Amgen, Thousand Oaks, Calif.

[*] Notice: The portion of the term of this patent subsequent to Dec. 10, 2002 has been disclaimed.

[21] Appl. No.: 501,024

[22] Filed: Jun. 4, 1983

[51] Int. Cl.$^4$ .................... A61K 37/26; C07K 7/06
[52] U.S. Cl. .................................. 514/4; 514/16; 530/329
[58] Field of Search .............. 260/112.5 R, 112.7; 424/178; 530/329; 514/4, 16

[56] References Cited

U.S. PATENT DOCUMENTS

| | | | |
|---|---|---|---|
| 2,843,525 | 7/1958 | Robinson et al. | 260/112.7 |
| 3,326,763 | 6/1967 | Antoniades et al. | 424/178 |
| 3,698,912 | 10/1972 | Winitz | 514/561 |
| 3,868,358 | 2/1975 | Jackson | 424/178 |
| 3,912,807 | 10/1975 | Alburn et al. | 424/178 |
| 3,941,763 | 3/1976 | Sarantakis | 260/112.5 LH |
| 4,107,158 | 8/1978 | LeFrancier | 424/178 |
| 4,125,606 | 11/1978 | Bornstein | 424/178 |
| 4,150,121 | 4/1979 | Dietze et al. | 424/178 |
| 4,558,033 | 12/1985 | Rudman | 514/4 |

OTHER PUBLICATIONS

IUPAC-1UB Commission on Biological Nomenclature, *The Journal of Biological Chemistry*, 247, No. 4, 977-983 (1972).
Yudave et al., *Biokhimiya*, 41(5), 843-846.
Rivier et al., 8th *American Peptide Symposium*, Tucson, Arizona, p. 237 (1983).
Chillemi, *J. Chem. Soc., Perkin Trans* 1(7), 1913-1917 (1981).
Morikawa et al., *Mol. Cell. Biol.*, 4(2) 228-231 (1984).
Vanderlaan et al., *J. Protein Chem.*, 2(4), 341-346 (1983).
Bornstein, review at pp. 41-44 in *Growth Hormones and Related Peptides* (A. Pecile, et al., eds.), Excerpta Medica, Amsterdam-Oxford. (1976).
Frigeri, et al., *Biochem. Biophys. Res. Comm.*, 91: 778-782 (1979).
Frigeri, et al., Proc. 64th Ann. Meeting of the Endocrine Society, San Francisco (Abstract 88), p. 101, Jun. 1982.
Goodman, *Metabolism*, 19:849-855 (1970).
Goodman, *Ann. N.Y. Acad. Sci.*, 148: 419-440 (1968).
Lewis, et al., *J. Biol. Chem.*, 253: 2679-2685 (1975).
Lewis, et al., *Biochem. Biophys. Res. Comm.*, 92: 511-516 (1980).
Lewis, et al., *Endocrine Res. Comm.*, 8: 155-164 (1981).
Sawyer, et al., *PNAS (U.S.A.)*, 77(10): 5754-5758 (1980).
Swislocki, et al., *Endocrinology*, 76: 665-672 (1965).
Yudaev, et al., *Biochem. Biophys. Res. Comm.*, 110: 866-872 (1983).
*Atlas of Protein Sequence and Structure*, vol. 5, Supp. 2, pp. 120-121 (M. Dayhoff, ed., National Biomedical Research Foundation, 1976).
Rudinger, pp. 1-7 in *Peptide Hormones*, Parsons (ed.), University Park Press, Baltimore (1976).

*Primary Examiner*—Johnnie R. Brown
*Assistant Examiner*—F. T. Moezie
*Attorney, Agent, or Firm*—Marshall, O'Toole, Gerstein, Murray & Bicknell

[57] ABSTRACT

Disclosed are novel synthetic peptides having primary structural homology to a continuous sequence of amino acid residues of human growth hormone in a region spanning positions thirty-two to forty-six ("hGH$_{32-46}$", or "deletion peptide"). In preferred forms, peptides of the invention comprehend: duplicate portions (i.e., sequence fragments) of hGH$_{32-46}$; stereochemical analogs and fragment analogs of hGH$_{32-46}$ including one or more amino acid residues in D-isomeric configuration; and, "interspecies" analogs and fragment analogs of hGH$_{32-46}$ including one or more non-homologous amino acid residues duplicating variant residues present in corresponding positions in corresponding regions of heterologous species growth hormones. Peptides of the invention are administered to mammals contemporaneously with exogenous insulin to generate hypoglycemic effects greater than available through administration of insulin alone. A presently preferred heptapeptide has the sequence, NH$_2$-Glu-Glu-Ala-Tyr-Ile-Pro-Lys-COOH, and has insulin-potentiating activity greater than hGH$_{32-46}$.

5 Claims, No Drawings

BIOLOGICALLY ACTIVE PEPTIDES STRUCTURALLY RELATED TO REGIONS WITHIN GROWTH HORMONES

BACKGROUND

The present invention relates generally to novel, biologically active synthetic peptides which are structurally related to a region within human growth hormone and which are active, inter alia, in potentiating the effects of insulin on glucose metabolism in mammals, including humans.

The diabetes mellitus disease state is a chronic disorder affecting carbohydrate, fat and protein metabolism. A characteristic feature of idiopathic diabetes mellitus is a defective or deficient insulin secretory response giving rise to impaired carbohydrate (glucose) use and resultant hyperglycemia. Two major variants of the disease state exist. One variant, seen in about ten percent of all idiopathic diabetics is referred to as insulin-dependent diabetes mellitus ("IDDM") or juvenile onset diabetes. This variant, frequently manifested for the first time in youth and is characterized by a progressive loss of insulin secretory function by beta cells of the pancreas and hence a progressive "dependence" on exogenous insulin for maintenance of carbohydrate metabolism. (This characteristic is shared by those non-idiopathic, or "secondary", diabetics whose disorders have their origins in pancreatic disease.) The second variant of idiopathic diabetes mellitus is referred to as non-insulindependent diabetes mellitus ("NIDDM") or adult onset diabetes and accounts for the remainder of the idiopathic diabetic population.

All diabetics, regardless of their genetic and environmental backgrounds or the age of onset of the disease, have in common an apparent lack of insulin or inadequate insulin function. Because transfer of glucose from the blood into muscle and fatty tissue is insulin dependent, diabetics lack the ability to utilize glucose adequately. Further, because glycogenolysis is ordinarily inhibited by insulin, the rate of glycogenolysis is elevated in the diabetic. Both these "derangements" from normal metabolic events lead to accumulation of glucose in the blood (hyperglycemia) to the point where renal glucose reabsorption capacity is exceeded and glycosuria occurs. The major source of energy for the diabetic thus becomes fatty acids derived from triglycerides stored in fatty tissue. In the liver, fatty acids are oxidized to ketone bodies which are circulated and used as an energy source by tissues. In the IDDM patient, and sometimes the NIDDM patient, the rate of formation of ketone bodies may exceed the rate of their utilization and ketosis along with metabolic acidosis may occur. Since tissues appear to be starving for glucose, dietary and tissue sources of protein are used in gluconeogenesis. Anabolic processes such as synthesis of glycogen, triglycerides and proteins are "sacrificed" to catabolic activities including glycogenolysis, gluconeogenesis and mobilization of fats. Thus, the diabetic state which has its origins as a "simple" insulin defect, results in widespread metabolic disturbances having long-term pathologic effects on nearly all organs and tissues of the body. Indeed, the diabetic state is one of the prime contributors to deaths caused by myocardial infarction, renal failure, cerebrovascular disease, atherosclerotic heart disease and systemic infections.

Diabetic therapy for IDDM patients and advanced NIDDM patients has consistently focused on administration of exogenous insulin derived from bovine and porcine sources. It is frequently the case that use of such heterologous species material gives rise to formation of anti-insulin antibodies which have activity-limiting effects and result in progressive requirements for larger doses in order to achieve desired hypoglycemic effects. This, combined with the generally progressive need of the IDDM patient for more exogenous insulin as beta-cell function is lost, tends to accelerate the pathologic effects of the diabetic state.

Use of the most common (and convenient) administrative route for exogenous insulin may itself exacerbate pathology resulting from insulin therapy. Subcutaneous injection of insulin gives rise to relatively high insulin levels in peripheral tissues and relatively low levels circulating through the liver, the primary site of endogenous insulin activity. High levels of insulin in peripheral tissue have been associated with blood vessel pathology (e.g., blood vessel constriction and permeability changes) and pathologic effects on associated peripheral tissues, e.g., diabetic retinopathy. The "swamping" effects of subcutaneously administered insulin on peripheral circulatory tissues eventually reduces the amount of insulin circulating to the liver—again resulting in the need for increased doses to achieve desired metabolic effects.

It will be apparent from the above that substantial long term benefits in insulin therapy for diabetics (especially IDDM patients) can be expected to attend the development of methods and materials for enhancing the hypoglycemic effects of exogenous insulin. If insulin therapy for a given patient is expected to continue over a period of decades, it is significant that initial doses be as small as possible and that large doses of exogenous insulin be avoided for as long as possible.

The recent past has seen modest advances in the development of chemical agents capable of stimulating endogenous insulin secretion and hence reducing the need for exogenous insulin in large doses. Further, recombinant DNA methods have been brought to bear on the problem of securing large scale production of homologous species (human) insulin with the hope that use of the "human" material will reduce the progressive need for larger doses of insulin resulting from the effects of anti-insulin antibodies made against heterologous species materials. As yet, however, no significant advances have been reported in research directed toward development of compounds which would function to augment hypoglycemic effects of any given dose of endogenous insulin and thus guarantee that the insulin dose regimen employed can always be set at or near the minimum needed for desired metabolic effect and will result in the minimum of adverse side effects. There continues to exist, therefore, a need in the art for methods and materials for enhancing the hypoglycemic effects of exogenous insulin in mammals, including humans.

Of interest to the background of the invention are the results of certain studies on insulin-like activities of human growth hormone ("hGH"). hGH is a relatively high molecular weight polypeptide (~22,000 Daltons) consisting of a continuous sequence of 191 amino acid residues with secondary structure provided by two disulfide bonds formed between cysteine residues at position numbers 53/165 and 182/189, respectively. ["Atlas of Protein Sequence and Structure," Vol. 5, Supp. 2, pp. 120-121 (M. Dayhoff, ed., National Biomedical Resarch Foundation, 1976)]. Early studies of the growth promoting effects of hGH revealed, as one of its intrinsic properties, the ability to initially raise and then lower blood levels of glucose and to lower free fatty acids within one hour of administration, followed by later increasing circulating fatty acids. See, e.g., Goodman, *Metabolism,* 19, pp. 849–855 (1970); Goodman, *Ann. N.Y. Acad. Sci.,* 148, pp. 419–440 (1968); and Swislocki, et al. *Endocrinology,* 76, pp. 665–672 (1965). The hyperglycemic and hypoglycemic effects of large doses of hGH are so pronounced in many cases that they constitute a substantial adverse side-effect of hGH therapy for growth disorders.

Determination of the effects of hGH on glycemia prompted a series of studies into the in vivo and in vitro actions of peptide fractions and synthetic fragments related to amino and carboxy terminal regions of hGH. See, e.g., the review by Bornstein appearing at pp.41–44 in "Growth Hormones and Related Peptides", A. Pecile, et al., eds. Excerpta Medica, Amsterdam-Oxford (1976). A variety of biological effects were noted including an insulin potentiating effect on glucose uptake by a fragment duplicating the sequence of amino acid residues at hGH positions 1 through 15 and a hyperglycemic effect for a peptide duplicating residues 176 through 191.

The discovery by Lewis, et al. in 1975 [*J.Biol.Chem.,* 253, pp. 2679–2685] of a naturally-occurring structural variant of hGH which differed from the major form of the hormone by having fewer amino acid residues prompted a systematic examination of the variant, 20,000 Dalton polypeptide, and its properties. Studies by Frigeri, et al., *Biochem. Biophys. Res. Comm.,* 91, pp. 778–782 (1979), Lewis, et al., *Biochem. Biophys. Res. Comm.,* 92, pp. 511–516 (1980), and Lewis, et al., *Endocrine Res. Comm.,* 8, pp. 155–164 (1981) established that the 20,000. Dalton variant lacked the hypoglycemic and fatty acid lowering effects of hGH but substantially retained its growth promotant effects. It was also determined that the "missing" amino acid residues were in a region spanning positions thirty-two to forty-six of hGH. Following these publications were reports of further studies directed toward ascertaining the role of the "missing" residues in the growth stimulating and insulin-like activities of hGH. Frigeri, et al., [Proc. 64th Ann. Meeting of the Endocrine Society, San Francisco, June 1982 (Abstract 88), p. 101] reported that, in normal rats, a synthetic peptide corresponding to residues 32 to 46 of hGH did not show either the late increases in free fatty acids nor the glycemic effects which are characteristic of intact hGH. An unspecified degree of improvement in glucose tolerance of a GT-impaired strain of mice (YS/Wf Nctr) was observed for the peptide, as was an in vitro increase in glucose utilization of insulin-stimulated fat cells of older obese rats. Yudaev, et al., *Biochem. Biophys. Res. Comm.,* 110, pp. 866–872 (1983) reported substantially the same in vitro effect on fat cells for a synthetic tetradecapeptide having a sequence of amino acids copying residues at positions 31 through 44, and reiterated an earlier report of the absence of any in vivo hypoglycemic effect for the tetradecapeptide in rabbits and normal rats. In sum, the above-noted studies revealed that while hGH displays substantial glycemic effects in vivo which are not shown by the 20,000 Dalton variant, the "missing" sequence had no glycemic effect in vivo unless provided to the test animal as part of the hGH polypeptide.

Also of interest to the present invention are recent studies revealing alteration of biological effects of relatively small synthetic peptides resulting from incorporation of amino acids in D-isomeric configuration rather than the naturally-occurring L-isomeric forms. See, e.g., Sawyer, et al., *P.N.A.S. (U.S.A.),* 77, pp. 5754–5758 (1980) relating to prolongation of effects of alpha-melanotropin through synthesis of the tridecapeptide with D-phenylalanine replacing L-phenylalanine in position 7. Finally, recent advances in recombinant DNA methods for securing large scale production of peptides and polypeptides have made possible the generation of analogs of naturally occurring substances which differ from the natural compounds in terms of the identity or location of one or more amino acid residues. Particularly interesting are those new compounds wherein variations in the sequence of residues are effected based on the identity of residues extant in heterologous species forms of the biologically active polypeptide or in differing subtypes of polypeptides within a family of related compounds. An example of the latter is the disclosure of the construction and use of analogs of human leukocyte interferons set out in co-owned, co-pending U.S. patent application Ser. No. 483,451, filed Apr. 15, 1983, by Alton, et al.

BRIEF SUMMARY

In one of its aspects, the present invention provides novel, biologically active synthetic peptides having primary structural homology to a continuous sequence of amino acid residues of human growth hormone ("hGH") in a region spanning positions thirty-two to forty-six, i.e., "hGH$_{32-46}$", NH$_2$-Glu-Glu-Ala-Tyr-Ile-Pro-Lys-Glu-Gln-Lys-Tyr-Ser-Phe-Leu-Gln-COOH.

A first class of peptides of the invention consists of peptide "fragments" having from three to fourteen amino acid residues in a sequence precisely duplicating a continuous portion of the above-noted region. Preferred peptides include the sequence of residues at positions 35 through 37 of hGH (i.e., have the sequence, RNH-Tyr-Ile-Pro-COR', wherein R is hydrogen or an amino acid residue and R' is hydroxyl or an amino acid residue) and a presently most preferred group of compounds have the sequence, NH$_2$-Glu-Glu-Ala-Tyr-Ile-Pro-Lys-COR', wherein R' is hydroxyl or an amino acid residue.

A second class of peptides of the invention consists of stereochemical analogs of hGH$_{32-46}$ or analogs of fragments of hGH$_{32-46}$ including as many as fifteen amino acid residues (analogs) or as few as three residues (fragment analogs) in which from one to three of the residues exist in a D-isomeric configuration and the remainder are in the L-isomeric form. Presently preferred compounds of this class include those wherein either a glutamic acid residue corresponding to the residue in position thirty-two of hGH$_{32-46}$ or an alanine residue corresponding to the residue at position thirty-four of hGH$_{32-46}$ is in D-isomeric form.

A third class of peptides of the invention consists of "interspecies" analogs of hGH$_{32-46}$ or analogs of fragments of hGH$_{32-46}$ including a sequence of three to fifteen amino acid residues in which one or more (and up to nine) residues present are not duplicative of residues present in hGH$_{32-46}$ but, rather, duplicate residues present in corresponding regions of heterologous species growth hormones (e.g., equine, ovine, bovine, murine/rat, and chicken growth hormones). Illustrative preferred peptides of this class include the heptapeptide having the sequence, NH$_2$-Glu-Arg-Thr-Tyr-Ile-Pro-Glu-COOH.

Also comprehended by the invention are stereochemical, interspecies analogs and fragment analogs of hGH$_{32-46}$.

In another of its aspects, the present invention provides improvements in insulin therapy methods for securing reduction in circulating glucose in mammals, including humans, which involve periodic parenteral administration of exogenous insulin. The improved methods comprise augmenting the effectiveness of insulin as a hypoglycemic agent by means of contemporaneous (e.g., simultaneous) administration of an effective amount of one or more of the above-noted novel peptides of the invention. Also comprehended by the present invention are novel pharmaceutical compositions including insulin and one or more peptides of the invention (in ratios of from about 1 mU insulin to 100 $\mu$g peptide to about 100 mU insulin to 1 $\mu$g peptide, and preferably about 1 mU insulin to 1 $\mu$g peptide along with a pharmaceutically acceptable diluent, adjuvant or carrier.

In another of its aspects, the present invention is seen to comprise a novel process for the formulation of (homologous or heterologous species) exogenous insulin-containing compositions for use in controlling the levels of circulating glucose in mammals wherein a selected desired hypoglycemic effect is determined to require the use of a predetermined quantity of insulin. According to the improved process, less than the predetermined quantity of insulin is incorporated but there is incorporated for contemporaneous administration an effective quantity of one or more peptides of the invention.

Other aspects and advantages of the present invention will be apparent upon consideration of the following detailed description of the invention including illustrative examples of the practice thereof. As employed therein and in the claims, the terms, "hGH$_{32-46}$", "deletion peptide", and "DP" shall be used synonymously to designate a peptide of the sequence: NH$_2$-Glu-Glu-Ala-Tyr-Ile-Pro-Lys-Glu-Gln-Lys-Tyr-Ser-Phe-Leu-Gln-COOH.

DETAILED DESCRIPTION

Incorporated by reference herein are the disclosures and detailed descriptions of co-owned, co-pending, contemporaneously-filed U.S. patent application Ser. No. 501,023, by co-inventor Christopher G. Rudman, entitled, "Potentiation of the Effects of Insulin by Peptides". Briefly put, the patent application relates to the discovery of unexpected physiological activity for a synthetic pentadecapeptide having an amino acid residue sequence duplicative of a region of residues spanning positions thirty-two through forty-six of human growth hormone. More specifically, it was discovered that while "deletion peptide" ("DP" or "hGH$_{32-46}$") lacked hypoglycemic effects in various model animal test systems the substance would, when contemporaneously administered with exogenous insulin, potentiate insulin activity and augment the hypoglycemic effectiveness of even quite small parenteral doses of insulin.

According to the present invention, three classes of novel peptides have been synthesized which have primary structural homology to deletion peptide. One class of peptides of the invention may be characterized as comprehending deletion peptide fragments, i.e., sequences of from three to fourteen amino acids which duplicate a continuous portion of the sequence of amino acid residues in deletion peptide. A second class of peptides of the invention comprehends stereochemical analogs and fragment analogs of hGH$_{32-46}$ which duplicate the amino acid residue sequence of deletion peptide or fragments thereof, but wherein from one to three amino acids are present in a D-isomeric configuration. Still a third class of peptides of the invention comprehends analogs and fragment analogs of DP which include one or more amino acid residues which are not homologous to human growth hormone. Rather, these residues are duplicative of residues extant at corresponding positions in corresponding regions of heterologous species growth hormones including equine, ovine, bovine, rat/murine and chicken species. Peptides of this class are herein referred to from time to time as "interspecies analogs".

Preliminary screenings of the biological activities of representative peptides of the invention has revealed, inter alia, a number of compounds which, at the doses tested, possess insulin potentiating activity. In at least one instance the activity displayed is substantially greater than that of deletion peptide, demonstrating utility of the compounds as a substitute for deletion peptide. Thus, in processes for formulating insulin-containing pharmaceutical compositions for use in controlling the levels of circulating glucose in a mammal wherein a selected desired reduction in circulating glucose is determined to require the use of a predetermined quantity of insulin, the present invention comprehends incorporating less than the predetermined quantity and incorporating for contemporaneous administration an effective amount of a peptide of the invention.

The following illustrative examples therefore relate to: (1) the synthesis of representative members of each of the three related classes of peptides of the invention; and, (2) tests for glycemic effects of peptides of the invention including, specifically, tests of the insulin potentiating activity of the compounds in various animal model systems.

EXAMPLE 1

Peptides of the present invention are all suitably manufactured according to the general method of Stewart, et al., *Solid Phase Peptide Synthesis*, (W. H. Freeman, San Francisco, 1969). Briefly put, peptides are constructed by means of a series of amino acid residue additions to an initial, column-bound residue selected to form the carboxy terminal residue of the peptide. Each selected carboxyl terminal amino acid is coupled to the polystyrene resin as a BOC-protected amino acid. All subsequent amino acid additions are carried out with dicyclohexylcarbodiimide using the appropriate BOC amino acid with side chain protecting groups as follows: Glutamic acid as the Y-benzyl ester; Tyrosine as O-2,6-dichlorobenzyl tyrosine; Lysine as 2-chlorobenzylcarbonyl lysine; Glutamine as xanthyl glutamine; and, Serine as O-benzyl serine. Finished protected peptides are cleaved from the resin with simultaneous deprotection using anhydrous HF. Individual peptides are purified by a combination of chromatography on Sephadex G10 and G25 or preparative thin layer chromatography. Desired products are isolated as stable lyophilized white to pale tan powders. Composition of peptides is determined by amino acid analysis after HCl digestion as described in "Protein Sequence Determination" page 197 (S. Needleman, ed., Springer-Verlag, 1975). Sequence verification is performed by automated amino acid analysis. Purified products migrate as a single spot on TLC. Rf values are determined with a pH 4–4.5 solvent comprising butanol, acetic acid, water and pyridine (15:3:12:10). Purity is further verified by reverse phase high pressure liquid chromatagraphy on a $C_{18} \mu$ bondapak column with a 0.1% trifluoroacetic acid-/acetonitrile gradient.

For purposes of illustration, thirteen representative peptides according to the invention are specified in Table I below, with the tabular presentation designed to readily display primary structural homology with the amino acid residues of $hGH_{32-46}$. Following the Table is a discussion of individual peptides and of their relationship to the three above-noted classes ("fragments", "stereochemical analogs" and "interspecies analogs") of compounds.

Peptide No. 8, 0.19.

B. Stereochemical Analogs of DP

Synthetic Peptide Nos. 9 and 10 illustrated in Table I comprise representative members of that class of compounds of the invention comprehending sequences of from 3 to 15 (and, preferably, from 4 to 12) amino acid residues which duplicate the sequence or a portion of the sequence of deletion peptide. Included in the sequence, however, are from one to three residues of amino acids in D-isomeric form, with the remainder being in L-isomeric form. The class is thus seen to include stereochemical analogs of $hGH_{32-46}$ as well as stereochemical analogs of fragments of $hGH_{32-46}$. Rf values for Peptide Nos. 9 and 10 are as follows: Peptide No. 9, 0.38; and

TABLE I

| Position No. | 32 | 33 | 34 | 35 | 36 | 37 | 38 | 39 | 40 | 41 | 42 | 43 | 44 | 45 | 46 |
|---|---|---|---|---|---|---|---|---|---|---|---|---|---|---|---|
| hGH Residues (15) | GLU | GLU | ALA | TYR | ILE | PRO | LYS | GLU | GLN | LYS | TYR | SER | PHE | LEU | GLN |
| Synthetic Peptide Residues | | | | | | | | | | | | | | | |
| No. 1 (4) | | | | TYR | ILE | PRO | LYS | | | | | | | | |
| No. 2 (5) | | | ALA | TYR | ILE | PRO | LYS | | | | | | | | |
| No. 3 (5) | | | | | | PRO | LYS | GLU | GLN | LYS | | | | | |
| No. 4 (6) | | GLU | ALA | TYR | ILE | PRO | LYS | | | | | | | | |
| No. 5 (6) | | | | | | | | | | LYS | TYR | SER | PHE | LEU | GLN |
| No. 6 (7) | GLU | GLU | ALA | TYR | ILE | PRO | LYS | | | | | | | | |
| No. 7 (9) | | | | TYR | ILE | PRO | LYS | GLU | GLN | LYS | TYR | SER | | | |
| No. 8 (12) | GLU | GLU | ALA | TYR | ILE | PRO | LYS | GLU | GLN | LYS | TYR | SER | | | |
| No. 9 (7) | GLU | GLU | ALA$^a$ | TYR | ILE | PRO | LYS | | | | | | | | |
| No. 10 (7) | GLU$^b$ | GLU | ALA | TYR | ILE | PRO | LYS | | | | | | | | |
| No. 11 (7) | GLU | GLU | ALA | TYR | ILE | PRO | GLU$^c$ | | | | | | | | |
| No. 12 (7) | GLU | ARG$^c$ | ALA | TYR | ILE | PRO | GLU$^c$ | | | | | | | | |
| No. 13 (7) | GLU | ARG$^c$ | THR$^d$ | TYR | ILE | PRO | GLU$^c$ | | | | | | | | |

$^a$D-Alanine
$^b$D-Glutamic Acid
$^c$Residue extant in equine, murine, rat, bovine, ovine, and chicken GH
$^d$Residue extant in bovine, ovine, and chicken GH

A. DP Fragments

Synthetic Peptide Nos. 1 through 8 illustrated in Table I comprise representative members of that class of peptides of the invention comprehending from 3 to 14 (and, preferably, from 4 to 12) amino acid residues which duplicate continuous sequences extant in the region spanning residues at positions thirty-two through forty-six of human growth hormone. Peptide Nos. 1, 2, 4, 6, 7, and 8 are representative of presently preferred compounds within this and all classes, i.e., those including the sequence of residues, -Tyr-Ile-Pro-, duplicating residues at positions thirty-five through thirty-seven of hGH. As discussed in detail, infra, one of the heptapeptides (Peptide No. 6) constitutes the presently preferred compound of the invention based on insulin potentiating effects. Rf values of Peptide Nos. 1 through 8 are as follows:

Peptide No. 1, 0.56;
Peptide No. 2, 0.47;
Peptide No. 3, 0.44;
Peptide No. 4, 0.28;
Peptide No. 5, 0.57;
Peptide No. 6, 0.38;
Peptide No. 7, 0.33; and, Peptide No. 10, 0.38.

C. Interspecies Analogs of DP

Synthetic Peptide Nos. 11 through 13 illustrated in Table I comprise representative members of that class of peptides of the invention comprehending sequences of from 3 to 15 (and, preferably, from 4 to 12) amino acid residues which duplicate partially (i.e., in terms of from 2 to 14 residues) the identity and relative position of residues in deletion peptide and wherein one or more of the non-homologous residues are selected from among residues at a corresponding position in a corresponding heterologous species growth hormone. Table II, below, illustrates the rationale for synthesis of peptides of this class by providing corresponding sequences of various species growth hormones. The $hGH_{32-46}$ sequence is set out in capital letters and homology to the hGH sequence in the heterologous species hormones is indicated by use of capital letters. Alignment of corresponding regions (comprehending residues at positions 33–47 of ovine and bovine species, and sequence residues at positions 32–46 of the remaining hormones) reveals that there is a total interspecies homology at six positions within the region. Development of interspecies analogs and fragment analogs is carried out in the context of consideration of the lack of homology at the remaining nine positions.

TABLE II

| GH Species | Position Nos. | Residues |
|---|---|---|
| Human | 32–46 | GLU—GLU—ALA—TYR—ILE—PRO—LYS—GLU—GLN—LYS—TYR—SER—PHE—LEU—GLN |
| Equine | 32–46 | GLU—Arg—ALA—TYR—ILE—PRO—Glu—Gly—GLN—Arg—TYR—SER—Ile—Gln—Asn |
| Murine/rat | 32–46 | GLU—Arg—ALA—TYR—ILE—PRO—Glu—Gly—GLN—Arg—TYR—SER—Ile—Gln—Asn |
| Bovine | 33–47 | GLU—Arg—Thr—TYR—ILE—PRO—Glu—Gly—GLN—Arg—TYR—SER—Ile—Gln—Asn |
| Ovine | 33–47 | GLU—Arg—Thr—TYR—ILE—PRO—Glu—Gly—GLN—Arg—TYR—SER—Ile—Gln—Asn |
| Chicken | 32–46 | GLU—Arg—Thr—TYR—ILE—PRO—Glu—Asp—GLN—Arg—TYR—Thr—Gln—Lys—Gln |

*Residue common to all species noted

As reflected by Table II, an interspecies analog of deletion peptide may include one or more and up to nine amino acid residues which are non-homologous to $hGH_{32-46}$. Interspecies fragment analogs of deletion peptide comprehend sequences of 3 to 14 (and preferably 4 to 12) residues which may include one or more (but correspondingly fewer than nine, depending on the fragment length) amino acid residues which are non-homologous to $hGH_{32-46}$. Peptide Nos. 11 through 13 of Table II are thus seen as representing interspecies fragment analogs of $hGH_{32-46}$ according to the invention, including one (e.g., Peptide No. 11) or more residues duplicative of residues extant at corresponding positions within a corresponding continuous sequence of residues of an heterologous species growth hormone.

While not specifically exemplified in Table I, peptides of the invention also include stereochemical, interspecies analogs and analog fragments wherein interspecies analogs and analog fragments as defined above additionally include from one to three amino acids in a D-isomeric configuration.

EXAMPLE 2

A series of experimental studies was conducted to ascertain biological effects (specifically the glycemic effects) of compounds of the invention. The protocols for these studies and the results obtained are set out below.

A. Insulin Potentiating Effects in Normal Rats

A study was conducted to determine insulin potentiating effects of Peptide Nos. 3, 5, and 6. Also tested was a dipeptide $NH_2$-Ile-Pro-COOH, a dipeptide outside the scope of the invention.

Test groups of 5 normal male Sprague-Dawley rats weighing about 200 grams were fasted for 18 hours and received (intraperitoneally in rapid succession) 1.0 ml of 0.75M glucose, and either 15 mU of insulin with 1% bovine serum ablumin in normal saline (pH 7.4) or a mixture of insulin as above with 25 μg Peptide Nos. 3, 5, 6 and dipeptide. Controls received only bovine serum albumin and saline. Blood was drawn after one hour and plasma glucose levels were determined.

The results of plasma glucose determinations (means ± standard error) are set out below in Table III and indicate that Peptide No. 6 is an exceptionally active insulin potentiator.

TABLE III

| Peptide No. | Plasma Glucose (mg/ml at 60 min.) | | |
|---|---|---|---|
| | Glucose Alone | Glucose + Insulin | Glucose + Insulin + Peptide |
| No. 3 | 162.0 ± 10 | 114.0 ± 7 | 110.0 ± 6 |

TABLE III-continued

| Peptide No. | Plasma Glucose (mg/ml at 60 min.) | | |
|---|---|---|---|
| | Glucose Alone | Glucose + Insulin | Glucose + Insulin + Peptide |
| No. 5 | 194.0 ± 21 | 128.0 ± 3 | 140.0 ± 19 |
| No. 6 | 150.0 ± 11 | 121.0 ± 28 | 52.0 ± 28 |
| $NH_2$—Ile—Pro—COOH | 165.0 ± 21 | 105.0 ± 15 | 95.0 ± 30 |

B. Insulin Potentiating Effects on Genetically Altered Mice at Differing Ages A study was conducted to ascertain insulin potentiating effects of Peptide Nos. 6, 9 and 10 on db/db mice aged 8 weeks and 14 weeks.

Test groups of 5 each of db/db mice weighing from 40 to 60 grams each were used. Glucose was administered intraperitoneally at a dosage of 0.1 ml/20 mg of a solution containing 135 mg/ml glucose. Insulin was intraperitoneally administered at a dose of 0.001 mU/10 g and Peptide Nos. 6, 9 and 10 were each simultaneously administered at a dose of 5 μg/10 g.

Plasma glucose determination generated by this study are set out in Table IV and again indicate significant effectiveness of Peptide No. 6.

TABLE IV

| Treatment | Plasma Glucose (mg/ml at 60 min.) | |
|---|---|---|
| | Age: 8 weeks | Age: 14 weeks |
| Glucose Alone | 189.0 ± 69 | 318.0 ± 25 |
| Glucose + Insulin | 135.7 ± 11 | 268.4 ± 65 |
| Glucose + Insulin + Peptide No. 6 | 92.3 ± 12 | 124.3 ± 34 |
| Glucose + Insulin + Peptide No. 9 | 90.8 ± 16 | 228.0 ± 38 |
| Glucose + Insulin + Peptide No. 10 | 111.0 ± 24 | 246.0 ± 43 |

C. Insulin-Potentiating Effects in Mice and Rats of Peptide No. 6 as Compared to DP A study was conducted to determine the relative insulin potentiating effects of Peptide No. 6 as compared to those of deletion peptide ("$hGH_{32-46}$").

Animals in test groups of five each were meployed in these procedures. Sprague-Dawley rats weighed approximately 200 grams; homozygous genetically abnormal mice (db/db and ob/ob) had weights in the range of 40 to 60 grams; heterozygous normal mice all weighed approximately 25 grams. Glucose was administered intraperitoneally at a dosage of 0.05 ml/0 g of a solution containing 135 mg/ml glucose, except for one group of rats which were given an oral dose of 1 ml of 270 mg/ml glucose solution. Insulin was intraperitoneally administered at a dose of 0.001 mU/10 g and both Peptide No. 6 and deletion peptide were administered were simultaneously administered at a dose of 5 μg/10 g.

Plasma glucose levels determined by this study are set out in Table V below and indicate that Peptide No. 6 was uniformly more effective in potentiating insulin effects than deletion peptide alone.

TABLE V

| Animal Model | Plasma Glucose (mg/ml at 60 min.) | | | |
|---|---|---|---|---|
| | Glucose Alone | Glucose + Insulin | Glucose + Insulin + hGH$_{32-46}$ | Glucose + Insulin + Polypeptide No. 6 |
| Mouse ob/ob | 222.0 ± 35 | 167.4 ± 26 | 138.2 ± 11 | 118.0 ± 20 |
| Mouse ob/+ (normal) | 120.0 ± 12 | 99.5 ± 6 | 56.0 ± 9 | 28.5 ± 5 |
| Mouse db/db | 320.0 ± 75 | 198.2 ± 31 | 134.0 ± 13 | 109.2 ± 22 |
| Mouse db/m (normal) | 99.0 ± 9 | 102.0 ± 10 | 49.0 ± 12 | 22.0 ± 10 |
| Rat (normal) | 150.0 ± 11 | 121.0 ± 28 | 73.0 ± 10 | 52.0 ± 6 |
| Rat* (normal) | 184.0 ± 14 | 144.0 ± 12 | 93.3 ± 14 | — |

*Glucose administered orally

D. Insulin Potentiating Effects in Primates of Peptide No. 6 as Compared to Deletion Peptide In a manner analogous to Study C, above, Peptide No. 6 and deletion peptide were studied for insulin potentiating effects in Rhesus monkeys. Blood samples were drawn from normal female monkeys (in four experimental groups of 3) five minutes before administration of an oral dose of 3.0 ml/kg of 0.5 g/ml glucose and intramuscular administration of either: (1) 0.5 ml/kg phosphate buffered saline (PBS), pH 7.4; (2) deletion peptide 0.1 ml/kg of 1.0 mg/ml solution in PBS; (3) deletion peptide as above combined with 0.5 ml/kg of 20 mU/ml insulin in PBS; or (4) insulin alone as above or (5) Peptide No. 6 0.1 ml/kg of a 0.5 mg/ml solution in PBS combined with insulin as above. Blood samples were then periodically withdrawn over two hours and analyzed for plasma glucose levels. Plasma glucose level data is set out in Table VI and reveals that insulin potentiating effects of Peptide No. 6 are essentially on par with, or superior on a weight basis to, those of deletion peptide under the conditions of the procedure.

TABLE VI

| Time | Plasma Glucose (mg/ml) | | | |
|---|---|---|---|---|
| | Glucose Alone | Glucose + Insulin | Glucose + Insulin + hGH$_{32-46}$ | Glucose + Insulin + Peptide No. 6 |
| −5 min. | 84.6 ± 7.5 | 71.0 ± 3.0 | 70.0 ± 2.5 | 72.0 ± 11 |
| +5 min. | 82.5 ± 6.2 | 79.0 ± 9.0 | 64.0 ± 4.0 | 62.0 ± 6.0 |
| +15 min. | 106.0 ± 14 | 72.0 ± 10 | 69.0 ± 9.0 | 69.5 ± 6.0 |
| +30 min. | 117.0 ± 16 | 85.0 ± 11 | 80.0 ± 5.3 | 68.0 ± 9.7 |
| +45 min. | 132.0 ± 13 | 88.0 ± 13 | 80.0 ± 5.9 | 73.0 ± 3.5 |
| +60 min. | 125.0 ± 12 | 109.0 ± 14 | 96.0 ± 8.0 | 79.0 ± 6.5 |
| +120 min. | 126.0 ± 12 | 108.0 ± 14 | 97.0 ± 6.6 | 88.0 ± 12 |

The foregoing illustrative examples are believed to establish with certainty that the hypoglycemic effects of exogenous insulin are substantially enhanced or potentiated when accompanied by contemporaneous administration with one or more peptides of the invention. While practice of the methods of the invention may comprehend contemporaneous parenteral administration of peptide prior to or subsequent to insulin administration, it is expected that the most highly augmentative effects will be observed by simultaneous administration of both. In this regard, it is expected that significant beneficial effects will attend parenteral (e.g., subcutaneous, intraperitoneal, intramuscular) administration of pharmaceutical compositions of the invention comprising admixtures of insulin and one or more peptides of the invention along with pharmaceutically acceptable diluents, adjuvants and carriers such as are commonly employed in administration of insulin alone. Suitable compositions are expected to result from use of admixtures of insulin and peptide in relative weight ratios varying from 1 mU insulin to 100 μg peptide to about 100 mU insulin to 1 μg peptide with a preferred ratio, based on the procedures of the above examples of about 1 mU insulin to 1 μg peptide.

While solid phase synthesis according to the procedures of Example 1 constitutes the presently preferred method for securing production of peptides of the invention in quantity, use of alternative methods such as liquid phase synthesis or microbial synthesis by recombinant DNA techniques (for all but the stereochemical analogs) is contemplated.

While the foregoing illustrative examples have necessarily concentrated on insulin potentiating biological effects of peptides, it will be understood that the absence of such effects in the experimental procedures practiced is not necessarily preclusive of potentiating utility at higher doses or utility in other physiological contexts, especially those involving carbohydrate fat and protein metabolism. It may be noted, for example, that ongoing studies of the in vivo biological activities of peptides of the invention have revealed preliminary evidence of insulin secretory stimulation effects, effects on levels of free fatty acids and effects on glucose uptake by hepatic and muscle tissue. The results of these studies indicate utility for the peptides used alone, for example, in diseases requiring stimulation of insulin secretion or depression of free fatty acids.

Numerous modifications and variations in practice of the present invention are expected to occur to those skilled in the art upon consideration of the foregoing detailed description of illustrative embodiments thereof. As one example, illustrative test procedures were conducted using individual peptides of the invention even though it is within the scope of the invention to employ such peptides either singly or in combination with others to develop desired biological effects. Consequently, only such limitations should be placed on the scope of the invention as appear in the appended claims.

What is claimed is:

1. A biologically active heptapeptide having the sequence, NH$_2$-Glu-Glu-Ala-Tyr-Ile-Pro-Lys-COOH.

2. A biologically active peptide having the sequence, NH$_2$-Glu-Glu-D-Ala-Tyr-Ile-Pro-Lys-COOH.

3. In the method for securing reduction of circulating glucose in humans by administering exogenous insulin, the improvement comprising concurrent administration of insulin and an amount of a heptapeptide of claim 2, said amount being effective in potentiating insulin.

4. A pharmaceutical composition effective for use in reducing levels of circulating glucose in humans, said composition comprising insulin and an amount of a heptapeptide of claim 1, said amount being effective in potentiating insulin.

5. A pharmaceutical composition according to claim 4 comprising insulin and heptapeptide in a relative weight ratio of from about 1 mU insulin to 100 μg heptapeptide to about 100 mU insulin to 1 μg heptapeptide.

* * * * *